US010314813B2

(12) United States Patent
Self (10) Patent No.: US 10,314,813 B2
(45) Date of Patent: Jun. 11, 2019

(54) ANTIMICROBIAL COMPOSITIONS FOR *CLOSTRIDIUM DIFFICILE*

(71) Applicant: University of Central Florida Research Foundation, Inc., Orlando, FL (US)

(72) Inventor: William T. Self, Oviedo, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

(21) Appl. No.: 15/946,070

(22) Filed: Apr. 5, 2018

(65) Prior Publication Data
US 2018/0325863 A1    Nov. 15, 2018

Related U.S. Application Data (60) Provisional application No. 62/482,133, filed on Apr. 5, 2017.

(51) Int. Cl.
| *A01N 31/08* | (2006.01) |
| *A01N 31/16* | (2006.01) |
| *A01N 43/16* | (2006.01) |
| *A01N 47/44* | (2006.01) |
| *A61K 35/00* | (2006.01) |
| *A61K 47/10* | (2017.01) |
| *A61K 47/18* | (2017.01) |
| *A61K 47/20* | (2006.01) |
| *A61K 47/22* | (2006.01) |
| *A61P 31/04* | (2006.01) |
| *A61K 31/055* | (2006.01) |
| *A61K 31/155* | (2006.01) |
| *A61K 31/353* | (2006.01) |

(52) U.S. Cl.
CPC ............ *A61K 31/353* (2013.01); *A01N 43/16* (2013.01); *A61K 35/00* (2013.01); *A61K 47/10* (2013.01); *A61K 47/18* (2013.01); *A61K 47/20* (2013.01); *A61K 47/22* (2013.01); *A61P 31/04* (2018.01); *A61K 31/055* (2013.01); *A61K 31/155* (2013.01); *A61K 2300/00* (2013.01)

(58) Field of Classification Search
None
See application file for complete search history.

(56) References Cited

FOREIGN PATENT DOCUMENTS

ES    2127690    4/1996

OTHER PUBLICATIONS

Amade, P., et al., Antimicrobial activities of marine sponges from french polynesia and brittany, "Marine Biology", pp. 223-228, vol. 70 (1982).
Bourguet-Kondracki, M., et al., Dipuupehedione a cytoxic new red dimer from a new caledonian marine sponge hyrtios sp, "Elsevier Science", pp. 3861-3864, vol. 37, Issue 22 (1996).
Bourguet-Kondracki, M., et al., Methanol adduct of puupehenone a biologically active derivative from the marine sponge hyrtios species, "J. Nat. Prod.", pp. 1304-1305, vol. 62 (1999).
Carte, B., Biomedical potential of marine natural products, "BioScience", pp. 271-286, vol. 46, Issue 4 (1996).
Freeman, J., et al., Antibiotics and Clostridium difficile, "Microbes and Infection", pp. 377-384, vol. 1 (1999).
Hagiwara, K., et al., Puupehenol a potent antioxidant antimicrobial meroterpenoid from a Hawaiian deep-water dactylospongia sp sponge, "J. Nat. Prod.", pp. 325-329, vol. 78 (2015).
Loo, V., et al., A predominantly clonal multi-institutional outbreak of clostridium difficile associated diarrhea with high morbidity and mortality, "N. Engl. J. of Med.", pp. 2442-2449, vol. 353, Issue 23 (2005).
Nasu, S., et al., Puupehenone-related metabolites from two hawaiian sponges hyrtios spp, "J. Org. Chem.", pp. 7290-7292, vol. 60 (1995).
Perez, M., et al., Antimicrobial action of compounds from marine seaweed, "Mar. Drugs" pp. 138, vol. 14, Issue 52 (2016).
Ravi, B., et al., Recent research in marine natural products: the puupehenone, "Pure & Appl. Chem.", pp. 1893-1900, vol. 51 (1979).
Robinson, S., et al., Using enzyme assays to evaluate the structure and bioactivity of sponge-derived meroterpenes, "J. Nat. Prod.", pp. 1857-1863, vol. 72 (2009).

*Primary Examiner* — Brian J Davis
(74) *Attorney, Agent, or Firm* — Timothy H. Van Dyke; Beusse, Wolter, Sanks & Maire PLLC (57) ABSTRACT

*Clostridium difficile* infects and kills 30,000-40,000 people a year in the United States. Provided herein are methods to inhibit growth and reduce the spread of *C. difficile* using puupehenone, a natural marine product that is excreted from some species of sponges and coral as a defense mechanism.

17 Claims, 5 Drawing Sheets

ANTIMICROBIAL COMPOSITIONS FOR
*CLOSTRIDIUM DIFFICILE*

BACKGROUND

Due to the both the emergence of antibiotic resistance and more virulent pathogens, there is a growing need for new antibacterial agents for use in clinical settings. Antibiotic resistance occurs in both gram-positive and gram-negative pathogens and generally arises within a hospital setting but can then spread to the general community. Multi-drug resistant and pandrug resistant gram-negative bacteria including *Acinetobacter baumanii, Escherichia coli, Klebsiella pneumoniae* and *Pseudomonas aeruginosa* pose the threat of untreatable infections. Current figures show that the number of deaths caused by methicillin-resistant *Staphylococcus aureus* (MRSA) infections is greater than that of HIV and tuberculosis combined and this has led to an increase in health-care costs due to MRSA which is estimated to be $3 billion to $4 billion per year. *Clostridium difficile*, a nosocomial pathogen is the etiologic agent for pseudomembranous colitis and can be fatal if not properly treated. Extension of hospitalization due to *C. difficile* infection has estimated costs of as much as 3.2 billion dollars per year. The virulence of *C. difficile* is on the rise and with rising numbers of infections in hospitals and long-term care facilities this organism has become one of the major public health threats of the $21^{st}$ century. The emergence of resistance coupled with the emergence of new, more virulent, pathogens demands the discovery of novel antibiotics.

*Clostridium difficile*: Nosocomial Pathogen
  Commonly known as a nosocomial pathogen that is linked to causing infectious diarrhea, colectomy or even death.
  Contains toxin A and B and has two chromosomal genes, TcdB and TcdA that activate these toxins by encoding them. TcdB enforces the binding of the cell, while TcdA causes cell death by interrupting the formation of the actin filament [4].
  Risks of manifesting *C. difficile*: antimicrobial exposure, age, and hospital stay. [2].]

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

Natural products are a proven resource for the discovery of clinically-relevant antibacterial agents however the rate of rediscovery of known compounds from terrestrial actinomycetes has shown the need to explore additional microbial biodiversity in diverse niches. Marine sponges host a large and diverse microbial population encompassing Bacteria, Archaea and microbial eukaryotes, many of which are unusual and rare microorganisms. Over the last 25 years we have developed an extensive culture collection of marine microbes (the Harbor Branch Marine Microbe Culture Collection, HBMMCC) with 70% of the collection derived from marine sponges. Preliminary screening of extracts from just a few isolates has identified actives against both MRSA and *C. difficile* confirming that the collection is an excellent source of natural products with activity against these pathogens.

*Clostridium difficile* infects and kills 30,000-40,000 people a year in the United States. In order to target and minimize the spread of *C. difficile* puupehenone, a natural marine product that is excreted from some species of sponges and coral as a defense mechanism, was screened for its antimicrobial properties. The minimum inhibitory concentration (MIC) of puupehenone was tested with respect to a strain of *C. difficile*, and then tested across multiple strains of the bacterium.

Puupehenone: Bioactive Marine Natural Product
  Marine natural product is a chemical found in the environment that exhibits some sort of biomedical activity [1].
  Marine microorganisms living in coral reefs manifest compounds and chemicals that are used as defense mechanism to maintain their niche.
  Puupehenone was proven on previous assays that their effective antimicrobial properties rely on its concentration [3].

It has now been discovered that Puupehenone, or derivatives thereof, and compositions containing same have remarkable antimicrobial activity. Specifically, it has been shown that Puupehenone has a potent antimicrobial activity on strains of *C. difficile*. Accordingly, certain embodiments herein relate to killing, inhibiting growth, or reducing a population of *C. difficile* bacteria involving subjecting the one or more *C. difficile* bacteria to a composition comprising puupehenone, or a derivative thereof at an effective amount to effect such killing, growth inhibition or reduction of the population. The term population includes one or more microbes. Alternatively, puupehenol is used as the active agent.

Other embodiments relate to a composition comprising a pharmaceutically acceptable carrier and an effective amount of a puupehenone compound. The term "puupehenone compound" as used herein refers to puupehenone or a derivative thereof, as well as a salt form of any of the foregoing. The use of "a" as an indefinite modifier to describe an embodiment or element of an embodiment shall include both singular and plural meaning (e.g. "a" puupehenone compound means one or more puupehenone compounds).

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

The puupehenone compounds described herein are useful for various non-therapeutic and therapeutic purposes. It is apparent from the testing that the puupehenone compounds are effective for killing, reducing amount of or inhibiting *Clostridium* (e.g. *C. difficile*) cell growth. Because of the antimicrobial properties of the puupehenone compounds, they are useful in a wide variety of settings including in vitro uses. They are also useful as standards and for teaching demonstrations. As disclosed herein, they are also useful prophylactically and therapeutically for treating *Clostridium* (e.g. *C. difficile*) infection in animals and humans.

Therapeutic application of the puupehenone compounds and compositions containing them can be accomplished by any suitable therapeutic method and technique presently or prospectively known to those skilled in the art. Further, the puupehenone compounds have use as starting materials or intermediates for the preparation of other useful compounds and compositions.

The dosage administration to will be dependent upon the type of host involved, its age, weight, health, kind of concurrent treatment, if any, frequency of treatment, and therapeutic ratio.

The disclosed puupehenone compounds can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

The composition could be formulated for non-patient uses (e.g. treating surfaces) or could be formulated with a carrier that is suitable for use on or in a patient. The composition could be administered parenterally, orally, intrarectally, topically, or other suitable modes of administration.

Therapeutic Uses

*Clostridium* is a genus of rod-shaped Gram-positive bacteria capable of producing endospores. The methods set forth herein can be used to treat the vegetative as well as the spore form of any *Clostridium* infection. Several *Clostridium* species are responsible for disease in humans. These include, but are not limited to, *Clostridium difficile* (*C. difficile*), *Clostridium botulinum* (*C. botulinum*), *Clostridium perfringens* (*C. perfringens*), *Clostridium tetani* (*C. tetani*) and *Clostridium sordelli* (*C. sordelli*).

*C. difficile* is the most serious cause of antibiotic-associated diarrhea and can lead to pseudomembranous colitis, a severe inflammation of the colon, often resulting from eradication of the normal gut flora by antibiotics. In a very small percentage of the adult population, *C. difficile* bacteria naturally reside in the gut. Other people accidentally ingest spores of the bacteria while they are patients in a hospital, nursing home, or similar facility. When the bacteria are in a colon in which the normal gut flora has been destroyed, for example, after a broad-spectrum antibiotic has been used, the gut becomes overrun with *C. difficile*. This overpopulation is harmful because the bacteria release toxins that can cause bloating, diarrhea and abdominal pain.

*C. botulinum* produces neurotoxins that cause the flaccid muscular paralysis seen in botulism.

*C. perfringens* is a common cause of food-borne illness, with poorly prepared meat and poultry the main culprits in harboring the bacterium. The *clostridium* perfingens enterotoxin (CPE) mediating the disease is heat-labile (inactivated at 74° C.) and can be detected in contaminated food, if not heated properly, and feces. Incubation time is between 6 and 24 (commonly 10-12) hours after ingestion of contaminated food. Often, meat is well prepared, but too far in advance of consumption. Since *C. perfringens* forms spores that can withstand cooking temperatures, if let stand for long enough, germination ensues and infective bacterial colonies develop. Symptoms typically include abdominal, cramping and diarrhea; vomiting and fever are unusual.

*C. tetani* usually enters a host through a wound to the skin and then it replicates. Once an infection is established, *C. tetani* produces two exotoxins, tetanolysin and tetanospasmin. Tetanospasmin released in the wound is absorbed into the circulation and reaches motor nerves all over the body. The toxin acts at several sites within the central nervous system including nerve terminals in the spinal cord, brain, peripheral nerves and autonomic nervous system. The clinical manifestations of tetanus are caused when tetanus toxin blocks inhibitory impulses, by interfering with the release of neurotransmitters. These inhibitory neurotransmitters inhibit the alpha motor neurons. With diminished inhibition, the resting firing rate of the alpha motor neuron increases, producing rigidity, unopposed muscle contraction and spasm. Characteristic features are risus sardonicus (a rigid smile), trismus (commonly known as "lock-jaw"), and opisthotonus (rigid, arched back). Seizures may occur, and the autonomic nervous system may also be affected. Hypertension and tachycardia alternating with hypotension and bradycardia may develop.

Not to be limiting, examples to provide for the administration of such dosages for the desired therapeutic treatment, may comprise between about 0.01% to 99.9%, or about 0.1% and 45%, and especially, about 1 and 15%, by weight of the total of one or more of the puupehenone compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Alternatively, the therapeutically effective amount of puupehenone, or derivative thereof, utilized in the compositions set forth herein can be, for example, a concentration greater of about 0.2% (w/w) and up to about 100% (w/w). For example, the therapeutically effective amount can be about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 15%, 20%, 25%, 30%, 35%, 40%, 45%, 50%, 55%, 60%, 65%, 70%, 75%, 80%, 85%, 90%, 95%, 100% or any percentage (w/w) in between the percentages set forth herein.

Provided herein is method of treating or preventing a *Clostridium* infection in a subject. The method comprises administering to the subject a composition with a therapeutically effective amount of puupehenone, or derivative thereof, wherein the subject has a *Clostridium* infection or is at risk of developing a *Clostridium* infection Further provided is a method of reducing the recurrence of a *Clostridium* infection in a subject. The method comprises administering to the subject a composition including a therapeutically effective amount of puupehenone, or derivative thereof, wherein the subject is at risk for recurrence of a *Clostridium* infection The *Clostridium* infection can be in the digestive tract, for example, in the stomach, small intestine, lower intestine or colon of a subject. The infection can also be in the central or peripheral nervous system or autonomic nervous system of a subject. A *Clostridium* infection can also be in the urinary tract of a subject. All strains are contemplated herein. A decrease or reduction of infection can occur in vitro, ex vivo or in vivo.

As utilized throughout, the term "infection" encompasses all phases of the *Clostridium* life cycle including, but not limited to, replication, spore formation, transition from a spore form of the bacteria to a vegetative form of the bacteria, toxin production and receptor-mediated cell entry of toxins.

As used herein, the term subject can be a vertebrate, more specifically a mammal (e.g., a human, horse, pig, rabbit, dog, sheep, goat, non-human primate, cow, cat, guinea pig or rodent), a bird, a reptile or an amphibian. The term does not denote a particular age or sex. Thus, adult and newborn subjects, whether male or female, are intended to be covered. As used herein, patient or subject may be used interchangeably and can refer to a subject with a disease or disorder. The term patient or subject includes human and veterinary subjects.

As used herein the terms treatment, treat, treating or ameliorating refers to a method of reducing one or more signs or symptoms of the disease or condition. Thus, in the disclosed method, treatment can refer to a 10%, 20%, 30%, 40%, 50%, 60%, 70%, 80%, 90%, or 100% reduction or amelioration in the severity of an established disease or condition, as evidenced by a reduction in one or more signs or symptoms of the disease or condition. For example, and not to be limiting, a method for treating a *Clostridium* infection is considered to be a treatment if there is a 10% reduction in one or more signs or symptoms of the infection in a subject as compared to control. For example, the method for treating a *Clostridium* infection is considered to be a treatment if there is a 10% reduction in one or more signs or symptoms of the *Clostridium* infection in a subject as compared to a control subject that did not receive a composition comprising a puupehenone compound described herein. Thus, the reduction can be a 10, 20, 30, 40, 50, 60, 70, 80, 90, 100%, or any percent reduction in between 10 and 100 as compared to control levels. It is understood that treatment does not necessarily refer to a cure or complete ablation of the disease, condition, or symptoms of the disease or condition.

A subject can also harbor *Clostridium* resulting in carriage of the bacteria, which can be asymptomatic. For example, the subject can harbor *Clostridium* spores that can germinate to become active, vegetative cells. Thus, also provided herein is a method of reducing *Clostridium* carriage comprising administering to the subject a composition comprising a therapeutically effective amount of a puupehenone compound, wherein the subject is a carrier or is at risk of becoming a carrier for *Clostridium*. In this method, a reduction in spore formation, a reduction in the number of spores and/or a reduction in the number of spores that germinate to become active, vegetative cells can occur. The reduction can be a 10%, 20%, 30%, 40%, 50%, 60%, 70%, 80%, 90%, or 100% reduction as compared to a control.

Further provided is a method of reducing the infectivity of *Clostridium* spores, comprising contacting a population of *Clostridium* spores with an effective amount of a puupehenone compound. In this method, the number of spores and/or the number of spores that germinate to become active, vegetative cells can be reduced. The reduction can be a 10%, 20%, 30%, 40%, 50%, 60%, 70%, 80%, 90%, or 100% reduction as compared to a control.

The population of spores can be an in vivo population or an in vitro population.

As utilized herein, by reducing the recurrence of a *Clostridium* infection is meant a method of preventing, precluding, delaying, averting, obviating, forestalling, stopping, or hindering the onset, incidence or severity of the reappearance of a *Clostridium* infection in a subject. As utilized herein, by reappearance of a *Clostridium* infection is meant the reappearance of one or more signs or clinical symptoms of a *Clostridium* infection after a period devoid of one or more clinical symptoms of a *Clostridium* infection. The recurrence of a *Clostridium* infection can be after treatment for a *Clostridium* infection, for example, after treatment of *C. difficile* with vancomycin, metronidazole and or fidaxomicin. The recurrence of a *Clostridium* infection can also be after a remission. A recurrence can occur days, weeks, months or years after treatment or after a remission. For example, the disclosed method is considered to reduce the occurrence of a *Clostridium* infection if there is a reduction or delay in onset, incidence or severity of the reappearance of a *Clostridium* infection, or one or more symptoms of a *Clostridium* infection in a subject at risk for a recurrence of a *Clostridium* infection compared to control subjects at risk for a recurrence of a *Clostridium* infection that did not receive a composition comprising a puupehenone compound disclosed herein. The disclosed method is also considered to reduce the recurrence of a *Clostridium* infection if there is a reduction or delay in onset, incidence or severity of the reappearance of a *Clostridium* infection, or one or more symptoms of a *Clostridium* infection in a subject at risk for recurrence of a *Clostridium* infection after receiving a composition comprising a puupehenone compound disclosed herein as compared to the subject's progression prior to receiving treatment. Thus, the reduction or delay in onset, incidence or severity of recurrence of a

*Clostridium* infection can be about a 10, 20, 30, 40, 50, 60, 70, 80, 90; 100%, or any amount of reduction in between.

In the methods set forth herein, a composition comprising a therapeutically effective amount of puupehenone compound can selectively inhibit *Clostridium* infection in the subject. By selective inhibition is meant that inhibition of *Clostridium* infection occurs while maintaining substantial survival of the natural flora in the digestive tract of the subject.

For the administration methods disclosed herein, each method can optionally comprise the step of diagnosing a subject with a *Clostridium* infection or at risk of developing a *Clostridium* infection. The method can also include assessing the effectiveness of the puupehenone compound containing composition and modifying the treatment regimen.

The compositions set forth herein can be provided in a pharmaceutical composition. The compositions include a therapeutically effective amount of the puupehenone compound in combination with a pharmaceutically acceptable carrier and, in addition, may include other medicinal agents, pharmaceutical agents, carriers, or diluents. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. By pharmaceutically acceptable is meant a material that is not biologically or otherwise undesirable, which can be administered to an individual along with puupehenone compound without causing unacceptable biological effects or interacting in a deleterious manner with the other components of the pharmaceutical composition in which it is contained.

The compositions comprising a therapeutically effective amount of puupehenone compound can be concurrently administered with another pharmaceutical agent (e.g. adjunctive antimicrobial agent) or agents. The pharmaceutical agent can be formulated with the therapeutically effective amount of a puupehenone compound in a single composition or can be formulated in a separate composition. The compositions comprising a therapeutically effective amount of puupehenone compound can also be administered subsequent to or prior to treatment with another pharmaceutical agent. For example, and not to be limiting, a composition comprising a therapeutically effective amount of puupehenone compound can be administered concurrently with, subsequent to, or prior to administration of vancomycin, metronidazole and/or fidaxomicin in order to treat, prevent or reducing the recurrence of *C. difficile*.

Any appropriate route of administration may be employed, for example, administration can be systemic or local. Systemic administration includes administration via injection or infusion. Other routes of administration, such as intranasal, dermal, aerosol, vaginal, rectal or oral administration are also contemplated. By pharmaceutically acceptable carrier is meant a material that is not biologically or otherwise undesirable, which can be administered to an individual along with the selected compound without causing unacceptable biological effects or interacting in a deleterious manner with the other components of the pharmaceutical composition in which it is contained.

Administration can be carried out using therapeutically effective amounts of the compositions described herein for periods of time effective to treat or reduce recurrence of a *Clostridium* infection. The effective amount may be determined by one of ordinary skill in the art and includes exemplary dosage amounts for a mammal of from about 0.5 to about 200 mg/kg of body weight of active composition per day, which may be administered in a single dose or in the form of individual divided doses, such as from 1 to 4 times per day. Such a dosing schedule can continue for days, weeks or months, depending on the subject and the type of infection. Alternatively, the dosage amount can be from about 0.5 to about 150 mg/kg of body weight of active composition per day, about 0.5 to 100 mg/kg of body weight of active composition per day, about 0.5 to about 75 mg/kg of body weight of active composition per day, about 0.5 to about 50 mg/kg of body weight of active composition per day, about 0.5 to about 25 mg/kg of body weight of active composition per day, about 1 to about 20 mg/kg of body weight of active composition per day, about 1 to about 10 mg/kg of body weight of active composition per day, about 20 mg/kg of body weight of active composition per day, about 10 mg/kg of body weight of active composition per day, or about 5 mg/kg of body weight of active composition per day.

According to the methods taught herein, the subject is administered an effective amount of a puupehenone compound. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J., polyethylene glycol (PEG), and PLURONICS™ (BASF; Florham Park, N.J.). Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Ranges may be expressed herein as from about one particular value, and/or to about another particular value. When such a range is expressed, this includes from the one particular value and/or to the other particular value. Similarly, when values are expressed as approximations, by use of the antecedent about, it will be understood that the particular value is disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

Adjunctive Antimicrobial Agents

The compositions disclosed herein may comprise puupehenone or a derivative thereof, with one or more adjunctive antimicrobial agents. For example, a composition may comprise puupehenone, or a derivative thereof, and one or more cationic antimicrobial agent. In certain non-limiting embodiments, the cationic antimicrobial agent(s) is (are) selected from the group consisting of quaternary ammonium antimicrobial compounds, antimicrobial biguanides, and combinations thereof. Quaternary ammonium antimicrobial compound, where present, is at a concentration between about 0.05 and 1% w/w, or between about 0.05 and about 0.5% w/w, or between about 0.1 and about 0.3% w/w, or between 0.1 and 0.23% w/w (if more than one species of quaternary ammonium antimicrobial compound is present, the foregoing are the concentration ranges of the total amount of all species present). Antimicrobial biguanide, where present, is at a concentration between about 0.05 and about 3.0% w/w, or between about 0.05 and 1.5% w/w, or between about 0.05 and about 1.0% w/w, or between about 0.05 and about 0.8% w/w, or between 0.05 and 0.5% w/w, or about 0.4% w/w; if more than one species of biguanide is present, the foregoing are the concentrations/ranges of the total amount of all species present.

Non-limiting examples of quaternary ammonium antimicrobial compounds that may be used include benzalkonium chloride (BZK), benzethonium chloride (BZT), dequalinium chloride, alkyldimethylbenzylammonium chloride, cetyl pyridinium chloride, methylbenzethonium chloride, cetalkonium chloride, cetrimonium chloride, cetyl trimethyl ammonium bromide (cetrimide) dofanium chloride, tetraethylammonium bromide, domiphen bromide, and combinations thereof.

Non-limiting examples of biguanides that may be used include chlorhexidine, as a free base or salt, polyhexamethylene biguanide ("PHMB"), alexidine, polyaminopropyl biguanide (e.g., Cosmocil CQ), and combinations thereof. Chlorhexidine salts that may be used include but are not limited to the following: chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidinedipro pionate, chlorhexidine di-iodobutyrate, chlorhexidine di-n-valerate, chlorhexidine dicaproate, chlorhexidine malonate, chlorhexidinesuccinate, chlorhexidine malate, chlorhexidine tartrate, chlorhexidine dimonoglycolate, chlorhexidine mono-diglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidinedicinnamate, chlorhexidine dimande late, chlorhexidine di-isophthalate, chlorhexidine di-2-hydroxy-napthoate, chlorhexidine embonate, and combinations thereof.

The compositions may further comprise one or more adjunctive antimicrobial agent that is not a cationic antimicrobial agent. Non-limiting examples of such additional agents include triclosan, parachlorometaxylenol ("PCMX"), chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, parachlorometaxylene, foscarnet, miconazole, fluconazole, itriconazole, ketoconazole, povidone iodine, combinations thereof and pharmaceutically acceptable salts thereof. For example, but not by way of limitation, phenoxyethanol, where present, may be at a concentration between about 0.1 and about 1% w/w, and triclosan, where present, may be at a concentration between about 0.025 to about 2% w/w, or between 0.15 and 1% w/w.

Another non-limiting example of an adjunctive antimicrobial which may be used is iodopropynylbutyl carbamate (IPBC; German plus), for example at a concentration between 0.05 and 2% w/w.

Cleaning Surfaces with Antiseptics

The puupehenone compound containing composition can be used to reduce microbial agents from the surface of a medical device such as a catheter, an endotracheal tube, a nephrostomy tube, a biliary stent, an orthopedic device, a prosthetic valve, a medical implant, dental devices or dental implants, cardiac assist devices, vascular grafts, tracheostomy, ventriclulostomy devices, or intrathecal devices. In some aspects, the catheter is an indwelling catheter such as a central venous catheter, a peripheral intravenous catheter, an arterial catheter, a Swan-Ganz catheter, a hemodialysis catheter, an urinary catheter, a peritoneal catheter, an umbilical catheter, a percutaneous nontunneled silicone catheter, a cuffed tunneled central venous catheter or a subcutaneous central venous port.

In other embodiments, methods are disclosed that are useful in reducing microbial agents from a surface such as an organic surface or an inorganic surface. An organic surface is exemplified by skin, surgical sutures, mucosal membrane surface, or an epithelial surface. An inorganic surface may be the surface of a pipe or pipeline, a floor, a table-top, a counter-top, hospital equipment, or a wheel chair, etc. Non-limiting examples of a pipe is an oil pipeline, a water pipeline, an ice machine pipe, or a beverage dispensing pipe.

It is contemplated that the antimicrobial or antiseptic solutions disclosed herein will find particular usefulness as antimicrobial mouthwash solutions. Such mouthwash solutions are contemplated to be useful both in conjunction with dental procedures and oral sterilization as well as in general dental and oral hygiene applications. Antimicrobial mouthwash is becoming extremely important in the prevention of oral cavity infections as well as aspiration pneumonia. Microbial organisms in the mouth particularly around the teeth, embed themselves in biofilm and the pathogenesis of infection and colonization is similar to that seen in, for example, vascular catheters. In this regard, it is contemplated that one will preferably apply a solution containing an alcohol (preferably ethanol) and a dipolar aprotic solvent (preferably DMSO) as a mouthwash or mouth flush solution. In certain embodiments, a second mouthwash can be used that contains a pleasant flavor (e.g., mint, menthol, etc) in order to reduce any possible lingering unpleasant tastes from the dipolar aprotic solvent (e.g., DMSO). Concentrations of an alcohol (preferably ethanol) for the mouthwash contemplated include from about 1% to about 35%, more preferably from about 5% to about 30%, and in certain embodiments from about 15% to about 27%. The dipolar aprotic solvent (e.g., DMSO) may be in the mouthwash at the same concentrations contemplated for antiseptic compositions or in lower concentrations. A second antimicrobial compound (e.g., triclosan) may also be present in the mouthwash. In certain embodiments, the toothpaste may contain about 0.5-5% DMSO, about 10% ethanol, and triclosan.

In other embodiments, antiseptics disclosed herein may be used in toothpaste in order to improve the antimicrobial properties of the toothpaste. The toothpaste would include a dipolar aprotic solvent (e.g., DMSO) at the same or a similar concentration as contemplated for antiseptic or mouthwash compositions. The toothpaste may or may not contain an alcohol (preferably ethanol). If present, the alcohol may be present at a concentration of from about 5% to about 15%, although concentrations of up to about 35% may be used in toothpastes. A second antimicrobial compound (e.g., triclosan) may also be present in the toothpaste.

Microorganisms that attach themselves to inert surfaces, such as medical devices including, vascular catheters, endotracheal tubes, Foley catheters, biliary stents, nephrostomy tubes, prosthetic valves, ventriculostomy or epidural catheters, or fluid pipelines, such as oil pipelines or water pipelines, produce a layer made of exopolysaccharide called microbial biofilm. These organisms embed themselves in this layer. This biofilm layer ultimately becomes the protective environment that shields these organisms on the inert surface from the antimicrobial activity of various antibiotics or antiseptics. In U.S. Pat. Nos. 5,362,754 and 5,688,516, incorporated herein by reference in their entirety, the present inventor demonstrated that a combination of one or more antimicrobial agent with one or more chelator and/or anticoagulant (such as EDTA or heparin) reduces or eradicates these antibiotic-resistant biofilm embedded microorganisms if the antimicrobial and chelator combination is allowed to dwell on the surface for at least 4 hours. However, in both clinical and environmental situations, it is typically not feasible to allow a 4 hour dwell time for the chelator and antimicrobial agent to reduce or eradicate the microbes. For example, it is not possible to interrupt the therapy of critically ill patients receiving continuous infusion therapy through a vascular catheter for 4 hours. It is also not possible to interrupt an environmental situation involving fluid pipelines for 4 hours to allow for such a prolonged dwell time of antimicrobial/chelator solution. In certain embodiments, an antiseptic solution can be applied to an inert surface or a medical device for a period of less than 4 hours and achieve substantial killing of microorganisms.

Packaging and Kits

Antimicrobial compositions comprising puupehenone or a derivative thereof may be included in a kit. For example, an antiseptic solution containing puupehenone and/or a derivative thereof may be provided in a kit to be administered as a catheter flush solution. In other embodiments, an antiseptic in a swab (e.g., as a Sepp or Frep). The kit will optionally include an instruction sheet insert to identify how the kit is to be used.

The kits may contain an puupehenone compound-containing antiseptic composition (e.g., present in a swab, present alone in a container means, etc). Additional components may also be present in the kit and/or in the antiseptic solution, such as for example, an antibiotic (e.g., minocycline), a chelator/anticoagulant (e.g., EDTA), or other antimicrobial agent. The kit may comprise of one or two or three or more compartments. The components of the kit may be provided in separate compartments or in the same compartment. The components of the kit may be provided separately or mixed. The mixed components may contain two or more agents such as an antibiotic, a chelator/anticoagulant or additional component.

In certain embodiments, an antiseptic solution may be combined with an additional powdered or non-liquid antimicrobial compound. In these embodiments, a Wet/Wet® dual chamber container system or a Liquid/Dry® dual container system, available from Becton-Dickinson, may be used in various disclosed embodiments where it is desirable to mix one or more component (e.g., antibiotic, chelator/anticoagulant, etc) with an antiseptic solution embodiment, typically just prior to use.

The container means of the kits will generally include at least one vial, test tube, flask, bottle, syringe or other container means, into which the antiseptic solution may be placed, and preferably, suitably aliquoted. Where an additional antibiotic or antimicrobial agent or additional component is provided, the kit may also contain a second, third or other additional container into which this component may be placed. The kit embodiments may also include a means for containing the antiseptic solution, antimicrobial agent, chelator/anticoagulant, and/or any other reagent containers in close confinement for commercial sale. Such containers may include injection or blow-molded plastic, or glass containers into which the desired vials are retained.

EXAMPLES

Example 1

Methods

Tests were performed in a Coy anaerobic chamber (Coy Labs Grass Lake, Mich.). The compound Puupehenone was dissolved in either methanol or DMSO for testing. Using a 96-well plate, 200 µL of BHIS media was added to 12 wells. One was the control (BHIS media alone). The sequential nine wells have increments of 5 µL of puupehenone. The remaining two wells have no puupehenone but one has 20 µL and another has 40 µL of methanol. These last wells are a separate test to determine if methanol influences the growth of C. difficile. Then 10 µL of C. difficile strain VPI 10463 or strain ATCC 9689 was added to each well except for the control. Trials with DMSO were performed in increments of 2 µL of puupehenone.

Effects of puupehenone on C. difficile were tested based on optical density (e.g. OD500 nm, OD600 nm or OD630 nm, inter alia) using an optical reader as is standard in the art.

Results

Figure 1:
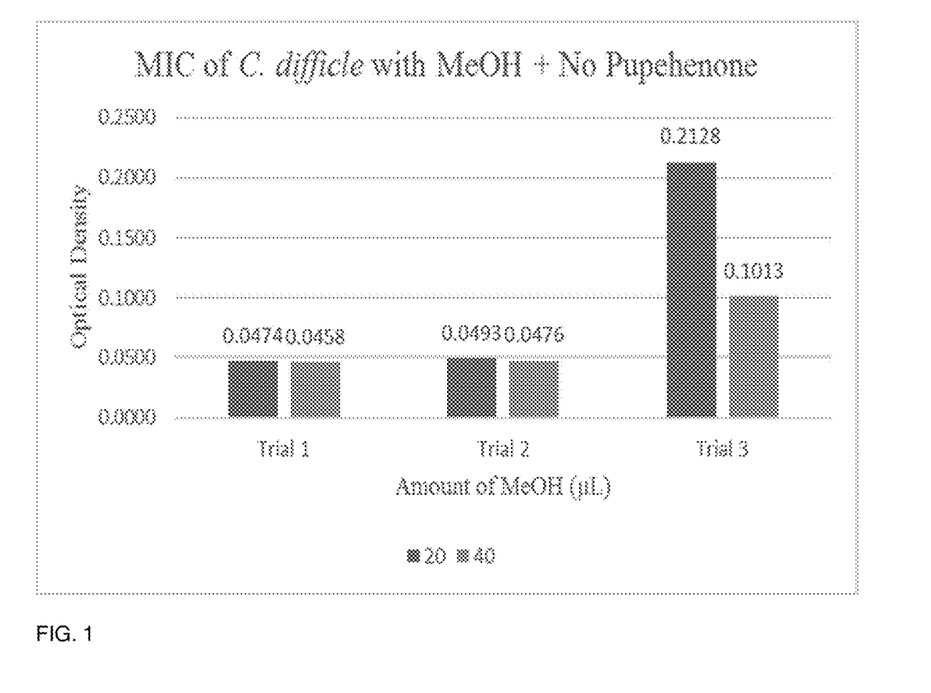
FIG. 1 shows a graph relating to determining of minimum inhibitory concentration study of a composition containing MeOH without puupehenone.
Figure 2:
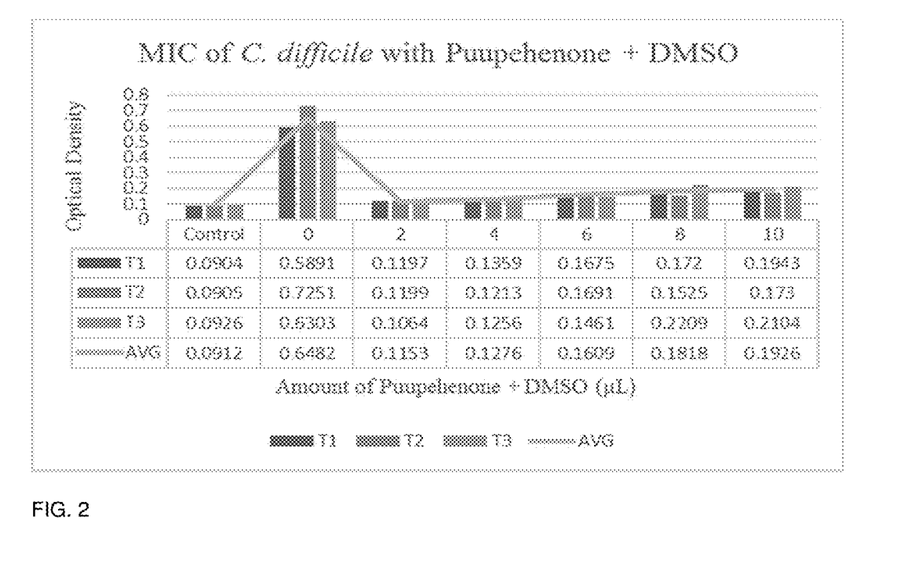
FIG. 2 shows a graph relating to determining of minimum inhibitory concentration study of a composition containing puupehenone and DMSO.
Figure 3:
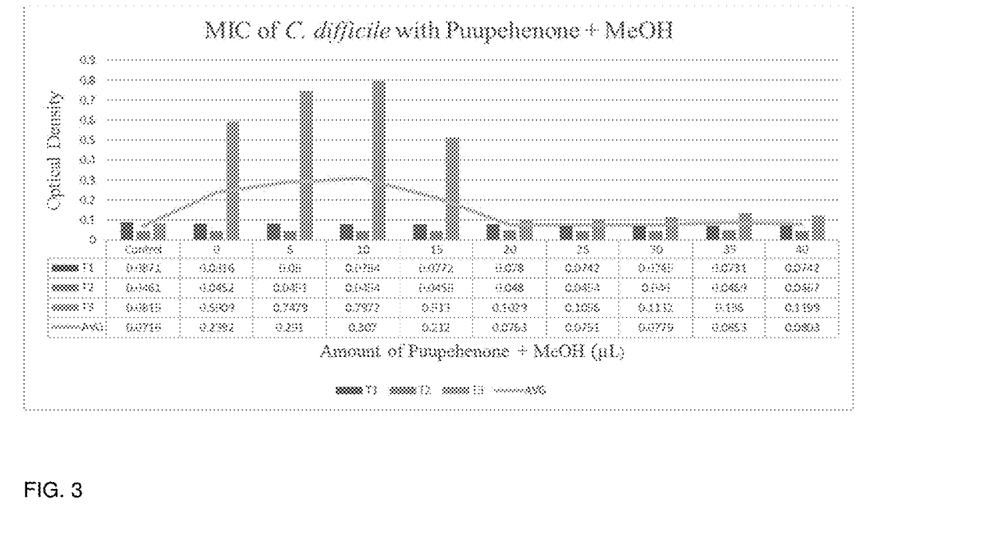
FIG. 3 shows a graph relating to determining of minimum inhibitory concentration study of a composition containing MeOH and puupehenone.
Figure 4:
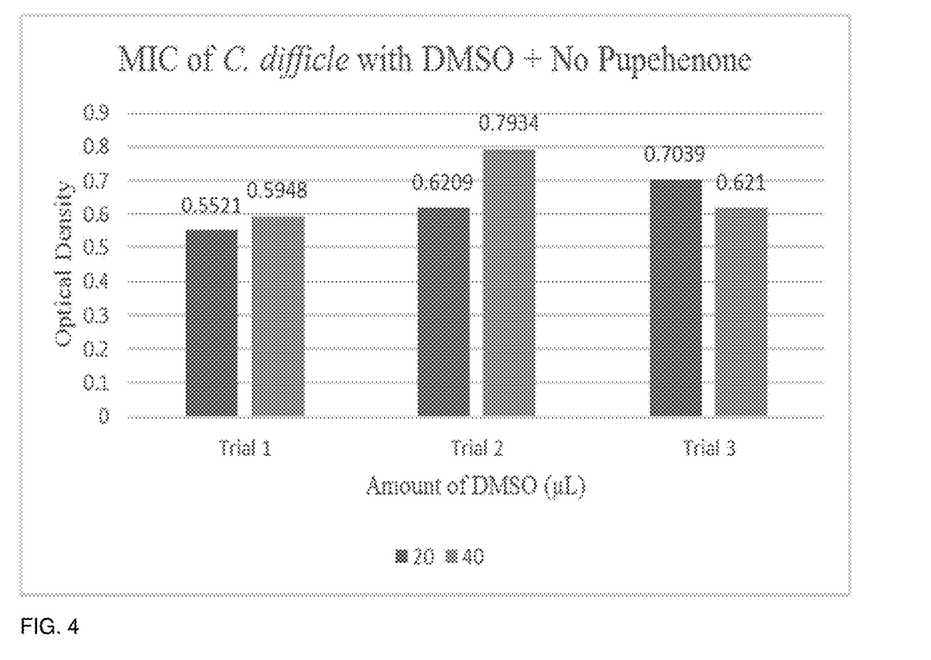
FIG. 4 shows a graph relating to determining of minimum inhibitory concentration study of a composition containing DMSO without puupehenone.
Figure 5:
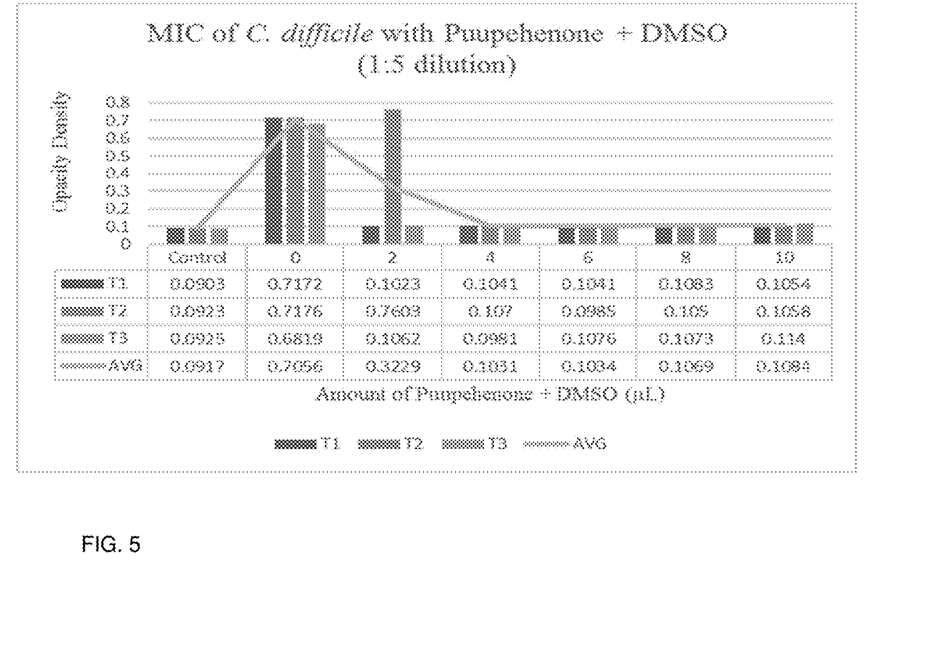
FIG. 5 shows a graph relating to determining of minimum inhibitory concentration study of a composition containing DMSO with puupehenone with 1:5 dilution.

MeOH showed a significant effect on the inhibition of Clostridium difficile. See FIG. 1. However, a separate test was performed with another solvent, DMSO and growth of C. difficile occurred. MIC tests with puupehenone+MeOH displayed potent antimicrobial activity throughout majority of trials. In Trial 1, 0 µL-well had 0.0816 (Trial 1). Then values gradually lowered throughout to 40 µL-well with a value of 0.0742. FIG. 3. MIC tests with puupehenone+DMSO exhibited inhibition of C. difficile. See FIG. 2. 0 µL-well confirmed growth of C. difficile on media with 0.5891 (Trial 1). See FIG. 4. Levels of growth dropped immensely afterwards. Another MIC test was taken with puupehenone but in a five-fold dilution. Puupehenone impact was still very potent. See FIG. 5.

Conclusion

Definite antimicrobial activity was demonstrated by puupehenone in the DMSO solvent challenge. Puupehenone showed very high potency, making lower concentrations suitable for efficacy. Secondarily, DMSO was shown to be a better solvent for puupehenone rather than methanol, since methanol also acts as an antimicrobial against C. difficile. The antimicrobial effect of puupehenone overcomes any effects of DMSO.

Those skilled in the art, based on the teachings herein will be able to:

Determine the minimum inhibition concentration of puupehenone in the smallest scale Perform a CLSI (Clinical and Laboratory Standards Institute) culture protocol Repeat multiple MIC tests on different type of C. difficile strains Perform MIC tests on related compounds Example 2 Serial Dilution of Puupehenone MIC experiments for Puupehenone were carried out in accordance with CLSI M11-A8 for broth dilutions. The levels of antimicrobial were achieved via serial dilution and listed as follows; 32 ug/mL, 16 ug/mL, 8 ug/mL, 4 ug/mL, 2 ug/mL, 1 ug/mL, 0.5 ug/mL, 0.25 ug/mL, 0.125 ug/mL, 0.0625 ug/mL/. Metranidazole was used a positive control. The only deviation from the CLSI was a modification to the media. For these experiments, it was necessary to remove the blood and hemin from the standard Brucella broth, as this decreased sensitivity to or activity of the compound. This was noted due to comparisons with previous BHIS experiments. Thus, the media was modified to resemble the BHIS media, with only Brucella broth mix (28 g/L) and yeast (5 g/L). The reason for the decreased efficacy of the drug when in blood based media is still being investigated. The MICs against different C. difficile strains (ATCC9689, NAP1027, and 630 were determined for both Puupehone and Matranidazole See Table 1.

TABLE 1

| | MIC (µg/mL) | |
| --- | --- | --- |
| Strain | Puupehenone | Metranidazole |
| Clostridium difficile ATCC 9689 | 4 | 0.25 |
| Clostridium difficile NAP1027 | 8 | 0.25 |
| Clostridium difficile 630 | 8 | 0.5 | n = 12 per strain/antimicrobial agent

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments. The teachings of any cited reference are incorporated herein in their entirety to the extent not inconsistent with the teachings herein.

REFERENCES

1. Carté, B. (1996). *Biomedical Potential of Marine Natural Products*. BioScience, 46(4), 271-286. doi:1.
2. Freeman, J. and Wilcox, M. (1999). *Antibiotics and Clostridium difficile*. Microbes and Infection, 1(5), 377-384.
3. Hagiwara, Kehau, Jaaziel E. Garcia Hernandez, and Mary K. Harper. (2015). Puupehenol, a *Potent Antioxidant Antimicrobial Meroterpenoid from a Hawaiian Deep-Water Dactylospongia sp. Sponge*. Journal of Natural Products 78, 325-28.
4. Loo, V. G. (2005, Dec. 8). *A Predominantly Clonal Multi-Institutional Outbreak of Clostridium difficile—Associated Diarrhea with High Morbidity and Mortality*. The New England Journal of Medicine, 24442-24449.

What is claimed is:

1. A method for killing, inhibiting growth, or reducing a population of *Clostridium* bacteria, the method comprising subjecting the population to a composition comprising puupehenone or puupehenol, or salt form thereof, at an effective amount to effect such killing, growth inhibition or reduction of the population.

2. The method of claim 1, wherein the composition comprises puupehenol.

3. The method of claim 1, wherein the composition comprises a carrier.

4. The method of claim 3, wherein the carrier comprises a polar aprotic solvent or an alcohol, or both.

5. The method of claim 3, wherein the carrier comprises an alcohol.

6. The method of claim 5, wherein the alcohol is selected from the group consisting of methanol, ethanol, n-propanol, isopropanol, n-butanol, isobutanol, n-pentanol, isopentanol, hexanol, heptanol, or isoamyl alcohol and a combination thereof.

7. The method of claim 1, wherein the composition comprises an adjunctive antimicrobial agent.

8. The method of claim 7, wherein the adjunctive antimicrobial agent is selected from the group consisting of chlorhexidine, chlorhexidine gluconate, triclosan; chloroxylenol and a combination thereof.

9. The method of claim 3, wherein the carrier is a polar aprotic solvent.

10. The method of claim 9, wherein the polar aprotic solvent is selected from the group consisting of dimethyl sulfoxide (DMSO), N,N dimethylacetamide (DMA), tetrahydrofuran, methyl ethyl ketone, ethyl acetate, acetonitrile, n,n-dimethylformamide (DMF), acetone, DMAC, NMP, a pyridine, and a combination thereof.

11. A method of treating or preventing a *Clostridium* infection in a subject, said method comprising administering to the subject a composition comprising a therapeutically effective amount of puupehenone or puupehenol, or salt form thereof, wherein the subject has a *Clostridium* infection or is at risk of developing a *Clostridium* infection.

12. The method of claim 11, wherein the infection is in the digestive tract of the subject.

13. The method of claim 11, wherein the *Clostridum* infection is a *C. perfingens* infection, *C. difficile* infection, *C. tetani* infection or a *C. botulinum* infection.

14. The method of claim 11, further comprising selecting a subject with a *Clostridium* infection or at risk of developing a *Clostridium* infection.

15. A method of reducing the recurrence of a *Clostridium* infection in a subject, comprising administering to the subject a composition comprising a therapeutically effective amount of puupehenone or puupehenol, or salt form thereof, wherein the subject is at risk for recurrence of a *Clostridium* infection.

16. The method of claim 15, wherein the infection is in the digestive tract of the subject.

17. The method of claim 15, wherein the *Clostridium* infection is a *C. difficile* infection.

* * * * *